United States Patent [19]

Sumner, Jr. et al.

[11] Patent Number: 5,334,754
[45] Date of Patent: Aug. 2, 1994

[54] PROCESS FOR PREPARING 2,5-DIPHENYLTEREPHTHALIC ACID BY OXIDATION

[75] Inventors: Charles E. Sumner, Jr.; Bruce L. Gustafson, both of Kingsport; Ernest W. Arnold, III, Blountville, all of Tenn.; Eric J. Fugate, Gate City, Va.; Dewey W. Fuller, Jr., Bristol, Tenn.

[73] Assignee: Eastman Chemical Company, Kingsport, Tenn.

[21] Appl. No.: 930,890

[22] Filed: Aug. 14, 1992

[51] Int. Cl.$^5$ .................. C07C 51/215; C07C 67/39
[52] U.S. Cl. ..................... 562/416; 560/77; 562/417; 562/480; 562/488; 568/630; 568/631; 568/928; 570/129; 570/182; 585/400
[58] Field of Search .......... 562/416, 417, 488, 480; 560/77; 568/630, 631, 928; 570/129, 182; 585/400

[56] References Cited

U.S. PATENT DOCUMENTS

| | | | |
|---|---|---|---|
| 2,833,816 | 5/1958 | Saffer et al. | 562/416 |
| 3,265,762 | 8/1966 | Quisenberry | 528/176 |
| 3,299,125 | 1/1967 | Ichikawa | 562/416 |
| 3,365,425 | 1/1968 | Watson | 528/176 |
| 3,723,518 | 3/1973 | Barone et al. | 562/417 |
| 4,098,817 | 7/1978 | Barone | 562/543 |
| 4,294,955 | 10/1981 | Harris, Jr. | 528/176 |
| 4,391,966 | 7/1983 | Harris, Jr. | 528/176 |
| 4,401,828 | 8/1983 | Tanger | 562/416 X |

FOREIGN PATENT DOCUMENTS 409437 1/1991 European Pat. Off. .
910484 11/1962 United Kingdom .

OTHER PUBLICATIONS

Weisburger, et al., *J. Org. Chem.*, 23, 1193, (1958).
Jones, *J. Chem. Res., Synop*, 10, 288, (1982).
Deuschel, *Helv. Chim. Acta*, 34, 2403, (1951).
Galpern et al., *Trudy Inst. Neft. Akad. Nauk. S.S.S.R.*, 12, 38, (1958).
Hickinbottom, *J. Chem. Soc.*, (1957), p. 4124.
Bodroux, *Am. Chim.*, 11, 511, (1929).
*Compt. rend.* 186, 1005, (1928).
*Chemische Berichte*, vol. 89, No. 12, (1956), Weinheim De, pp. 2794–2799, F. Ebel et al. 'Trans–Fluorenacendion, Ein Neues, Verkupbares Diketon'.

*Primary Examiner*—José G. Dees
*Assistant Examiner*—Vera C. Clarke
*Attorney, Agent, or Firm*—Bernard J. Graves, Jr.

[57] ABSTRACT

Provided is a process for preparing 2,5-diphenylterephthalic acid, which is useful in preparing certain polyesters, especially liquid-crystalline polyesters. In this process, p-xylene is di-alkylated with cyclohexene to provide 2,5-dicyclo-hexyl-p-xylene, which is in turn dehydrogenated to provide 2,5-diphenylxylene. 2,5-Diphenylxylene is then oxidized to provide 2,5-diphenylterephthalic acid by utilization of a cobaltous/manganous/bromide oxidation system.

5 Claims, No Drawings

PROCESS FOR PREPARING 2,5-DIPHENYLTEREPHTHALIC ACID BY OXIDATION

FIELD OF THE INVENTION

This invention belongs to the field of synthetic organic chemistry. In particular, the present invention relates to a method for preparing 2,5-diphenylterephthalic acid.

BACKGROUND OF THE INVENTION

It is known that 2,5-diphenylterephthalic acid is useful as a monomer in the preparation of liquid-crystalline polyesters. U.S. Pat. No. 3,365,425, describes polyesters prepared from ethylene glycol, terephthalic acid, and an asymmetrically substituted phthalic acid selected from 2,5-diphenylterephthalic acid, 4,6-diphenylisophthalic acid, and 5-t-butylisophthalic acid. In this patent, the 2,5-diphenylterephthalic acid is prepared by treatment of p-xylene with cyclohexene in the presence of $AlCl_3$ to provide 2,5-dicyclohexy-p-xylene, which is then dehydrogenated over 5% Pd/C and oxidized with $KMnO_4$. (See also, F. Ebel and W. Deuschel, Chem. Ber., 89, 2794 (1956) and E. K. Weisburger and J. H. Weisburger, *J. Org. Chem.*, 23, 1193 (1958).)

SUMMARY OF THE INVENTION

The present invention provides a process for preparing 2,5-diphenylterephthalic acid, which is useful in preparing certain polyesters, especially liquid-crystalline polyesters. In this process, p-xylene is di-alkylated with cyclohexene to provide 2,5-dicyclohexyl-p-xylene, which is in turn dehydrogenated to provide 2,5-diphenylxylene. 2,5-Diphenylxylene is then oxidized to provide 2,5-diphenylterephthalic acid utilizing a cobalt-/manganese/HBr oxidation system.

DETAILED DESCRIPTION OF THE INVENTION

The present invention provides a process for preparing 2,5-diphenylterephthalic acid, optionally substituted with one group selected from $C_1$–$C_{10}$ alkyl, halo nitro or a group of the formula —$CO_2R^4$ or —$OR^4$, wherein $R^4$ is $C_1$—$C_4$ alkyl; which comprises (a) di-alkylation of a compound of the formula

wherein $R^3$ is hydrogen, $C_1$—$C_{10}$ alkyl, halo, nitro, or a group of the formula —$CO_2R^4$ or —$OR^4$ wherein $R^4$ $C_1$—$C_4$ alkyl; with cyclohexene in the presence of an acid catalyst, to provide a compound of the formula

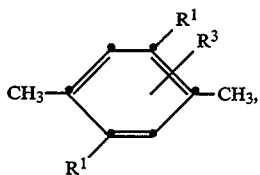

wherein $R^1$ is cyclohexyl; followed by (b) deydrogenation to provide a compound of the formula

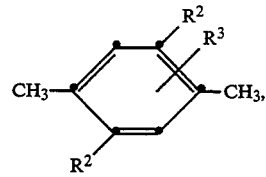

wherein $R^2$ is phenyl; followed by (c) oxidation in the presence of air or oxygen and a cobaltous bromide oxidation catalyst system, at a temperature of about 75° C. to 250° C., and at a pressure of about 10 to 1000 psig.

In the above process step (a), the acid catalyst may be selected from a variety of acids including, for example, phosphoric acid, sulfuric acid, methanesulfonic acid, trifluoromethanesulfonic acid, polyphosphoric acid, acidic molecular sieves, $SiO_2/Al_2O_3$, p-toluenesulfonic acid, trichloroacetic acid, dichloroacetic acid, trifluoroacetic acid, aluminum trichloride, aluminum tribromide, boron trifluoride, and acidic resins such as AMBERLYST™ 15, AEROCAT™, and the like. Preferred catalysts include the acidic resins.

As noted above, $SiO_2/Al_2O_3$ can be used as an acidic catalyst, in either a crystalline or amorphous form. In this regard, preferred catalysts include medium and large pore size silica/alumina catalysts such as the hydrogen Y form type zeolite catalysts. Typical examples include DAVISON Y-20, Y-72, Y-74, and Y-84.

In step (a), p-xylene is preferably used as both solvent and reactant; in this fashion, unreacted p-xylene can be recovered and recycled.

The cyclohexene reactant can be used as such or generated in situ from a precursur such as cyclohexanol.

The alkylation step may be carried out over a wide range of reaction conditions. Preferred temperatures are between about 0° and 300° C. preferred reaction pressures between about 0.01 and 30 atmospheres, and contact times in the range of about 0.01 to about 30 hours. Following alkylation, the intermediate product (2,5-dicyclohexyl-p-xylene) may be recovered by conventional isolation techniques, for example, by extraction, distillation, and the like.

The dehydrogenation step (b) may be carried out under a variety of conditions, preferably in the presence of a dehydrogenation catalyst. It is believed that any catalyst (or reaction conditions) which is operable for the conversion of cyclohexene or cyclohexane to benzene will be suitable for use in the practice of this step. Examples of suitable dehydrogenation catalysts include Group VIII and Group IB metals, as well as additional modifying components such as elemental sulfur, alkali metals, and the early transition metals (i.e., Group IVA, V, VIA, and VIIA metals). Preferred modifiers include sulfur and copper. Among the preferred catalysts are the noble metals. For ease of catalyst handling and to minimize catalyst expense, it is also preferred to use a supported catalyst, especially on carbon. The process may be operated using either a fixed bed or slurry system.

Examples of preferred dehydrogenation catalysts include sulfided palladium on alumina, sulfided palladium on carbon, sulfided platinum on carbon, palladium-copper on carbon support, palladium on alumina, platinum on alumina, modified Pt/Pd mixtures on silica, alumina, or carbon and the like.

In the dehydrogenation step, the preferred temperature range is from about 100° C. to about 500° C., preferred pressure in the range of about 0.01 to about 30 atmospheres, with contact times in the range of about 0.01 to about 36 hours. Further preferred temperatures are from about 225° C. to 350° C. and pressures from about 0.01 to 1 atmosphere.

When dehydrogenation catalyst is employed, the dehydrogenation reaction can be conducted in either batch or continuous mode. When carried out in batch mode, the substrate to catalyst weight ratio employed typically falls within the range of about 10:1 up to 1000:1, with a substrate to catalyst weight ratio of about 20:1 up to 100:1 being preferred.

When carried out in continuous mode, the substrate to catalyst weight ratio will vary as a function of reactant space velocity, catalyst loading level, reactor design, and the like.

The use of solvent in the dehydrogenation step is optional. When employed, solvents which are stable under the dehydrogenation conditions are suitable, and are employed in amounts ranging from 10 up to 90 weight percent of the reaction mixture. Examples of suitable solvents include biphenyl, naphthalene, diphenylether, tetralin, durene, prehnitene or 1,2,3,4-tetramethylbenzene, and the like.

The catalyst utilized may be recycled from the slurry by filtering the hot reaction mixture. The filtration may be conducted at the reaction temperature, above the melting point of the reaction mixture or at a temperature between about 100° C. and 200° C. A preferred range of temperatures for recovering the catalyst by filtration is between 125° C. and 150° C.

In a preferred embodiment of the invention, hydrogen gas produced as a result of the reaction is removed from the reaction atmosphere as the reaction proceeds. This can be accomplished by a variety of techniques as are well known by those of skill in the art. For example, the removal of hydrogen gas can be attained by circulating an inert gas through the atmosphere immediately above, or directly into, the reaction mixture. By means of example, the inert gas may be nitrogen. However, other unreactive gases may also be utilized for the removal of the hydrogen gas. As one alternative, hydrogen gas can be removed by careful addition of a purge gas containing small amounts of a reactive gas, e.g., oxygen, which enables the removal of hydrogen as water.

The net result of hydrogen gas removal is to shift the equilibrium concentration from the starting material or substrate to the product of the reaction by removing from the system any amount of hydrogen produced.

Following dehydrogenation, the desired product (2,5-diphenyl-p-xylene) can be recovered by conventional techniques, such as, for example, by crystallization, extract, distillation, precipitation and the like.

In a preferred embodiment of the present invention, the alkylation stage and the dehydrogenation stage can be integrated in such a fashion that by-product streams from the alkylation and dehydrogenation stages can be recovered and recycled for conversion to additional quantities of desired products. Similarly, unreacted cyclohexyl-p-xylene can be recycled to the dehydrogenation stage and subjected to additional treatment under dehydrogenation conditions.

2,5-Diphenyl-p-xylene can be readily oxidized to diphenylterephthalic acid in the presence of air or oxygen using selected catalysts. These oxidations are generally conducted at temperatures in the range of about 75° to about 250° C. with the preferred range being about 90° to about 150° C. Air pressures of about 10 to about 1000 psig are useful with 150–400 air being preferred.

The oxidation reactions are generally conducted in low molecular weight aliphatic acids such as acetic, propionic, butyric acid and the like. Acetic acid is a preferred solvent and generally about 10 to 90% of the reaction charge is solvent.

Highly useful catalysts for this oxidation process include those based on the cobalt/manganese/bromide system. Zirconium compounds may be used instead of the manganese moiety if desired or instead, only cobalt/bromide may be utilized. Useful forms of these catalyst components include the organic acid salts of the metals such as cobalt acetate, cobalt propionate, cobalt butyrate, cobalt benzoate, cobalt toluate or the corresponding manganese or zirconium salts and the like. The bromide component of the catalyst is generally hydrogen bromide. The diphenylterephthalic acid product may be purified by extraction, precipitation, or recrystallization procedures. Purification can also be achieved by converting the diphenylterephthalic acid to an ester such as the methyl or ethyl ester followed by suitable distillation, extraction, precipitation, or recrystallization procedures.

As a further aspect of the present invention, there is provided a process for preparing 2,5-diphenylterephthalic acid, which comprises oxidizing 2,5-diphenyl-p-xylene in the presence of a Cobaltous bromide oxidation system.

Experimental Section

EXAMPLE 1

Preparation of 2,5-Dicyclohexy-p-xylene p-Xylene (50 g, 0.47 moles), 2 g (0.024 moles) of cyclohexene and 1 g of Y-20 zeolite catalyst were placed in a 250 mL, 3-neck flask fitted with a stirrer and water condenser. The flask was purged with nitrogen and the reaction mixture heated until refluxing began at 126° C. Cyclohexene was added in 2 g increments and the reflux temperature gradually increased to 141° C. A total of 48 g (0.58 mole) of cyclohexene was added during a total reaction time of 7 hours.

After cooling the reaction mixture to 25° C., it was filtered to remove the solid catalyst and then distilled through a 1 inch diameter glass column with 22 inches of Goodloe packing. p-Xylene and monocyclohexyl-p-xylene were removed by stripping at reduced pressure. Material remaining in the distillation pot was the desired product, (2,5-dicyclohexyl-p-xylene) and it was recrystallized from acetone to provide 74.8 g of 2,5-dicyclohexyl-p-xylene with Tm of 184–187° C.

EXAMPLE 2

Preparation of 2,5-Dicyclohexyl-p-xylene p-Xylene (3 kg, 28.3 moles) was added to a 12 l 3-neck flask. With stirring, 40 g of AlCl₃ were added to the flask. The flask is cooled externally with an ice bath and the temperature of the reaction mixture was decreased to 12° C. Cyclohexene was added to the reaction mixture from a dropping funnel at a rate which was constantly adjusted to maintain the reaction temperature in the range of 20° to 25° C. A total of 2800 mL (2270 g, 27.6 moles) of cyclohexene were added during the 90 minute reaction period. A total of 500 mL of water was added with stirring to deactivate the AlCl₃ catalyst. The aqueous layer was separated from the organic layer and then the organic layer was washed two more times with 1:1 portions of water. After removing the water layer, 40 g of anhydrous CaCl₂ were added with stirring to dry the organic layer. After 15 minutes stirring, the organic layer containing the 2,5-dicyclohexyl-p-xylene was decanted from the calcium chloride. Assay of the crude reaction mixture by G. C. showed it to contain 8.0 area % p-xylene, 43.8 area % cyclohexyl-p-xylene and 48.2 area % 2,5-dicyclohexyl-p-xylene.

The reaction mixture was distilled through a 1-inch diameter glass column containing 22 inches of Goodloe packing. Solvent and low boiling impurities were stripped off and a small forecut was taken before collecting 2308 g of cyclohexyl-p-xylene at 200° C./120 torr. Material remaining in the distillation pot was recrystallized from acetone to provide 2540 g of 2,5-dicyclohexyl-p-xylene.

EXAMPLE 3

Dehydrogenation of 2,5-Dicyclohexyl-p-xylene

To a 3-liter three neck flask fitted with a stirrer, Vigreux column (1 inch × 12 inches), condenser, and distillation head were added 90.0 g (wet weight, 53% water) of 5% sulfided Pd/C catalyst and 610 g of n-propanol. The reaction mixture was heated to reflux (base temperature 111° C.) and the water/n-propanol azeotrope was removed at a head temperature of 95° C. After all water was removed from the system, the reaction mixture was cooled to less than 100° C. and 540.9 g (2.0 moles) of 2,5-dicyclohexyl-p-xylene were added. Cold water to the condenser was stopped and 15 psi steam was passed through the condenser. The reaction mixture was heated by means of a heating mantle until the base temperature was 246° C. (head temperature was at 209° C.) and material was foaming in the flask. The reaction was continued for 4.5 hours with the base temperature gradually increasing to 275° C. and the head temperature up to 259° C.

The heating mantle was removed and steam was removed from the condenser and the reaction mixture allowed to cool to room temperature under a nitrogen atmosphere. About 500 ml of toluene was added to the reaction mixture and it was then filtered to remove catalyst. The solution was distilled through a 1-inch diameter column containing 22 inches of Goodloe packing. After removing solvent and low boiling impurities, 465 g of product (2,5-diphenyl-p-xylene) remain in the distillation pot. This material was recrystallized from acetone.

EXAMPLE 4

Oxidation of 2,5-Diphenyl-p-xylene

Into a 2 liter Hastelloy autoclave were placed 1000 mL of acetic acid, 84 g (0.33 moles) of 2,5-diphenyl-p-xylene, 8.0 g of cobalt acetate tetrahydrate, 2.0 g of manganese acetate, 6.0 g of 48% hydrogen bromide, and 50 mL of water. The reaction vessel was sealed, heated to 100° C. and pressured to 350 psig with air while the reaction mixture was being stirred. Air and nitrogen continually fed to the autoclave at 3.0 standard liters per minute. The reaction was maintained under these conditions for 5 hours. The reaction mixture was removed from the autoclave and cooled in a wet ice bath. The solid product (crude 2,5-diphenylterephthalic acid) was recovered by filtration. Analysis by liquid chromatography indicates a yield of 57% was obtained. The crude 2,5-diphenylterephthalic acid was recrystallized from isobutyric acid to provide a colorless product (mp 301–304° C.).

We claim:

1. A process for preparing 2,5-diphenylterephthalic acid, optionally substituted with one group selected from the group consisting of $C_1$–$C_{10}$ alkyl, halo, nitro, a group of the formula —$CO_2R^4$, and —$OR^4$, wherein $R^4$ is $C_1$–$C_4$ alkyl; which comprises (a) di-alkylation of a compound of the formula

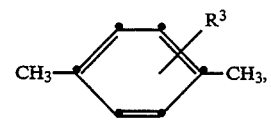

wherein $R^3$ is hydrogen, $C_1$–$C_{10}$ alkyl, halo, nitro, or a group of the formula —$CO_2R^4$ or —$OR^4$, wherein $R^4$ is $C_1$–$C_4$ alkyl; with cyclohexene in the presence of an acid catalyst, to provide a compound of the formula

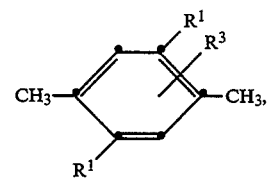

wherein $R^1$ is cyclohexyl; followed by (b) dehydrogenation in the presence of a Group VIII or Group IB catalyst, at a temperature of about 100° C. to 500° C., and at a pressure of about 0.01 to 30 atmospheres, to provide a compound of the formula

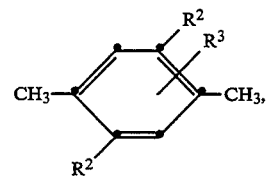

wherein $R^2$ is phenyl; followed by (c) oxidation in the presence of air or oxygen and a cobaltous bromide oxidation catalyst system, at a temperature of about 75° C. to 250° C., and at a pressure of about 10 to 1000 psig.

2. The process of claim 1, wherein the oxidation system further comprises Mn or Zr.

3. The process of claim 1, wherein the cobalt is in the form of a salt selected from a list consisting of cobalt acetate, cobalt propionate, cobalt butyrate, cobalt benzoate, and cobalt toluate.

4. The process of claim 2, wherein the manganese is in the form of a salt selected from a list consisting of manganese acetate, manganese propionate, manganese butyrate, manganese benzoate, and manganese toluate.

5. The process of claim 2, wherein the zirconium is in the form of a salt selected from a list consisting of zirconium acetate, zirconium propionate, zirconium butyrate, zirconium benzoate, and zirconium toluate.

* * * * *